US011789002B2

(12) United States Patent
Park et al.

(10) Patent No.: US 11,789,002 B2
(45) Date of Patent: Oct. 17, 2023

(54) MANAGING APPARATUS FOR FOOD INFORMATION AND MANAGING METHOD FOR FOOD INFORMATION

(71) Applicant: INDUSTRY-UNIVERSITY COOPERATION FOUNDATION HANYANG UNIVERSITY ERICA CAMPUS, Ansan-si (KR)

(72) Inventors: Taejoon Park, Seoul (KR); Dae Han Ahn, Seoul (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 258 days.

(21) Appl. No.: 16/895,113

(22) Filed: Jun. 8, 2020

(65) Prior Publication Data
US 2020/0303054 A1 Sep. 24, 2020

Related U.S. Application Data

(63) Continuation of application No. PCT/KR2018/015507, filed on Dec. 7, 2018.

(30) Foreign Application Priority Data

Dec. 8, 2017 (KR) .................. 10-2017-0167887
Dec. 4, 2018 (KR) .................. 10-2018-0154523

(51) Int. Cl.
| | |
|---|---|
| *G01N 33/02* | (2006.01) |
| *G16H 20/60* | (2018.01) |
| *G06N 20/00* | (2019.01) |
| *G01N 21/25* | (2006.01) |
| *G06V 20/68* | (2022.01) |

(Continued)

(52) U.S. Cl.
CPC ............ *G01N 33/02* (2013.01); *G01N 21/25* (2013.01); *G06N 20/00* (2019.01); *G06V 10/58* (2022.01); *G06V 10/82* (2022.01); *G06V 20/68* (2022.01); *G16H 20/60* (2018.01); *G06F 2218/12* (2023.01)

(58) Field of Classification Search
CPC ........ G16H 20/60; G06N 20/00; G01N 21/25; G01N 33/02; G06K 9/00536
USPC ........................................... 705/2
See application file for complete search history.

(56) References Cited

U.S. PATENT DOCUMENTS

| | | | |
|---|---|---|---|
| 7,048,768 B1 | 5/2006 | Rouse et al. | |
| 7,101,347 B2 | 9/2006 | Culhane et al. | |
| 2017/0176255 A1* | 6/2017 | Nciri | ..................... G01J 3/0224 |

FOREIGN PATENT DOCUMENTS

| | | |
|---|---|---|
| JP | 2006-329965 A | 12/2006 |
| JP | 2015-215273 A | 12/2015 |
| KR | 10-2006-0122941 A | 11/2006 |

(Continued)

OTHER PUBLICATIONS

International Search Report for PCT/KR2018/015507 dated Apr. 8, 2019 [PCT/ISA/210].

*Primary Examiner* — Daniel A Hess
(74) *Attorney, Agent, or Firm* — Sughrue Mion, PLLC (57) ABSTRACT

The managing apparatus for food information according to one embodiment of the present invention provides database of spectral signals according to caloric nutrient concentrations based on spectral signals of standard model food randomly prepared according to caloric nutrient concentrations.

6 Claims, 9 Drawing Sheets

(51) Int. Cl.
 G06V 10/82 (2022.01)
 G06V 10/58 (2022.01)

(56) References Cited

FOREIGN PATENT DOCUMENTS

KR   10-2012-0044200 A   5/2012
KR   10-2016-0061586 A   6/2016
WO      2017/150214 A1   9/2017

* cited by examiner

| Standard model food | Caloric nutrient (N_S) | | | Spectral signal (S_S) |
|---|---|---|---|---|
| | Carbohydrate | Protein | Fat | |
| Standard model food 1 | 5 | 0 | 0 | Spectral signal 1 |
| Standard model food 2 | 5 | 5 | 0 | Spectral signal 2 |
| Standard model food 3 | 5 | 5 | 5 | Spectral signal 3 |
| ... | ... | ... | ... | ... |
| Standard model food n | x | x | x | Spectral signal n |

| Reference food | Caloric nutrient (N_R) | | | Spectral signal (S_R) |
|---|---|---|---|---|
| | Carbohydrate | Protein | Fat | |
| Reference food 1 | 15 | 8 | 7 | Spectral signal 1 |
| Reference food 2 | 85 | 30 | 7 | Spectral signal 2 |
| Reference food 3 | 40 | 22 | 30 | Spectral signal 3 |
| ... | ... | ... | ... | ... |
| Reference food n | x | x | x | Spectral signal n |

MANAGING APPARATUS FOR FOOD INFORMATION AND MANAGING METHOD FOR FOOD INFORMATION

BACKGROUND OF THE INVENTION

1. Field of the Invention

The present invention relates to a managing apparatus for food information and a managing method for food information, and more particularly, to a managing apparatus for food information and a managing method for food information to autonomously learn a spectrum signal of food.

2. Description of the Prior Art

A conventional scheme for analyzing food mainly includes a chemical food analysis and a non-destructive food analysis.

The chemical food analysis has the highest accuracy by actually extracting a sample of food and measuring a chemical reaction of the sample, but is available only at a laboratory level, and it takes a very long time in the special case such as cultivation of microorganisms.

In contrast, the non-destructive ingredient analysis refers to a scheme of analyzing a spectrum of reflected light after irradiating food with light of a normal camera (visible area), a near-IR (infrared area) or the like, and it is meaningful in that the food may be non-destructively analyzed and results may be quickly provided.

The non-destructive ingredient analysis has a limit because a measured input is compared with data stored in advance in a previously constructed database to output a result, and thus the reliability of food analysis is lowered when a new inquiry is inputted before a database is incompletely constructed.

Therefore, the inventors of the present invention have invented a managing apparatus for food information and a managing method for food information in which the disadvantages of the existing non-destructive ingredient analysis are improved.

SUMMARY OF THE INVENTION

The present invention provides a managing apparatus for food information and a managing method for food information to construct a database of spectral signals corresponding to ingredients of caloric nutrients by machine learning scheme.

The present invention further provides a managing apparatus for food information and a managing method for food information to have high-precision machine learning results.

The present invention still further provides food information on a spectral signal for a predetermined food based on a spectral signal database.

The technical problems to be solved by the present invention are not limited thereto.

The managing apparatus for food information according to one embodiment of the present invention includes: a standard model food spectral information acquisition unit for acquiring a standard spectral signal corresponding to each standard model food and caloric nutrient information for each standard model food, in which the standard model food is set to have concentrations of carbohydrate, fat, and protein according to a predetermined criterion; a reference food spectral information acquisition unit for acquiring a spectral signal corresponding to each reference food and caloric nutrient information for the reference food; a learning unit for learning a scheme of generating a spectral signal from the synthesized caloric nutrient information such that a difference between a spectral signal generated by synthesizing the caloric nutrient information of the standard model food and a spectral signal of a reference food corresponding to the synthesized caloric nutrient information is a predetermined standard or below; and a database for storing a spectral signal for a newly combined caloric nutrient based on a learning result of the learning unit.

According to one embodiment, when a spectral signal for a specific food is acquired after the learned result is stored in the database, a food information providing unit for providing food information corresponding to the spectral signal for the specific food through the database may be further included.

According to one embodiment, when the spectral signal for the specific food is not stored in the database, the food information providing unit may generate a caloric nutrient combination that generates a spectral signal for the specific food through the learning unit.

According to one embodiment, the food information providing unit may take a learning spectral signal, which matches the spectral signal for the specific food, into consideration in the database in which the matching degree may vary according to a type of food information to be provided.

According to one embodiment, the matching degree in the case that the food information is name information of the specific food may be higher than the matching degree in the case that the food information is information on a caloric nutrient of the specific food.

The managing method for food information according to one embodiment of the present invention includes: a standard model food spectral information acquisition step of acquiring a standard spectral signal corresponding to each standard model food and caloric nutrient information for each standard model food, in which the standard model food is set to have predetermined concentrations of carbohydrate, fat, and protein; a reference food spectral information acquisition step of acquiring a spectral signal corresponding to each reference food and caloric nutrient information for the reference food; a learning step of learning a spectral signal corresponding to the synthesized caloric nutrient information such that a difference between a spectral signal generated by synthesizing the caloric nutrient information of the standard model food and a spectral signal of a reference food corresponding to the synthesized caloric nutrient information is a predetermined standard or below; and a database construction step of storing a spectral signal for a newly combined caloric nutrient based on a result of the learning step.

The managing apparatus for food information according to one embodiment of the present invention includes a reference food spectral information acquisition unit for acquiring a spectral signal corresponding to each reference food and caloric nutrient information for the reference food; a learning unit for learning a relationship between a spectral signal and a caloric nutrient through a learning network based on the acquired spectral signal and the acquired caloric nutrient information; and a database for storing a spectral signal for a newly combined caloric nutrient based on a learning result of the learning unit, wherein the learning network may include a common network that receives and processes a spectral signal corresponding to the reference food, and a caloric nutrient-specific network following the common network and composed of an individual caloric nutrient.

According to one embodiment, a joint layer may be located between the common network and the caloric nutrient-specific network, and the number of nodes in the joint layer may be less than the number of nodes in a layer prior to the joint layer.

According to one embodiment, the joint layer may be connected to a verification network, in which the verification network may inversely generate the inputted spectral signal based on the result from the common network, and the learning unit may retrain the common network when the degree of matching between the inputted spectral signal and the inversely generated spectral signal is a predetermined criterion or below.

According to one embodiment, the learning unit may determine the degree of matching between the inputted spectral signal and the inversely generated spectral signal, based on a waveform of the spectral signal.

According to one embodiment, when a predetermined spectral signal is acquired, a food information providing unit for providing food information matching the predetermined spectral signal based on the database may be further included.

According to one embodiment, the food information providing unit may differently apply the matching degree according to a type of provided food information, in which the matching degree in the case that the food information is name information of food may be higher than the matching degree in the case that the food information is information on a caloric nutrient of the food.

The managing method for food information according to one embodiment of the present invention includes a reference food spectral information acquisition step of acquiring a spectral signal corresponding to each reference food and caloric nutrient information for the reference food; a learning step of learning a relationship between a spectral signal and a caloric nutrient through a learning network, based on the acquired spectral signal and the acquired caloric nutrient information; and a database construction step of storing a spectral signal for a newly combined caloric nutrient, based on a result of the learning step, wherein the learning network may include a common network that receives and processes a spectral signal corresponding to the reference food, and a caloric nutrient-specific network following the common network and composed of an individual caloric nutrient.

According to one embodiment of the present invention, the managing apparatus for food information and the managing method for food information can construct a spectral signal database corresponding to ingredients of a caloric nutrient by using a machine learning scheme.

According to one embodiment of the present invention, a database having high precision can be provided through a self-validation According to one embodiment of the present invention, food information having highly reliability can be provided by only using a predetermined spectral signal.

Technical effects to be improved according to the present invention are not limited to the above-described advantageous effects.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION OF THE EXEMPLARY EMBODIMENTS

Hereinafter, preferred embodiments of the present invention will be described in detail with reference to the accompanying drawings. However, the technical spirit of the present invention is not limited to the embodiments, but may be realized in different forms. The embodiments introduced here are provided to sufficiently deliver the spirit of the present invention to those skilled in the art so that the disclosed contents may become thorough and complete.

When it is mentioned in the specification that one element is on another element, it means that the first element may be directly formed on the second element or a third element may be interposed between the first element and the second element. Further, in the drawings, the thicknesses of the membrane and areas are exaggerated for efficient description of the technical contents.

Further, in the various embodiments of the present invention, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments illustrated here include their complementary embodiments. Further, the term "and/or" in the specification is used to include at least one of the elements enumerated in the specification.

In the specification, the terms of a singular form may include plural forms unless otherwise specified. Further, the terms "including" and "having" are used to designate that the features, the numbers, the steps, the elements, or combination thereof described in the specification are present, and may be understood that one or more other features, numbers, step, elements, or combinations thereof may be added. Further, in the specification, the expression 'a constant length' or 'the same length' may be understood as meaning 'a substantially constant length' or 'substantially the same length'.

Further, in the following description of the present invention, a detailed description of known functions and configurations incorporated herein will be omitted when it may make the subject matter of the present invention unnecessarily unclear.

Figure 1:
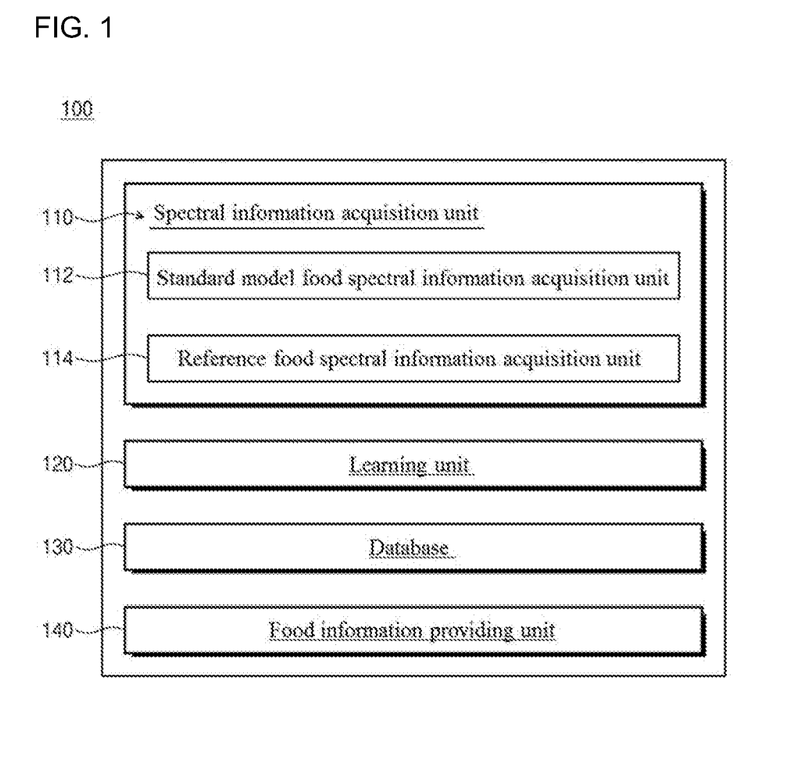
FIG. 1 shows a block diagram of a food information managing apparatus according to a first embodiment of the present invention.

FIG. 1 is shows a block diagram of a food information managing apparatus according to a first embodiment of the present invention.

When a spectral signal for a predetermined food is given, a food information managing apparatus 100 according to one embodiment of the present invention may provide information on the predetermined food, such as a name, calories, a content of each caloric nutrient, and the like of the food by taking into consideration that spectral signals (hyperspectral images) exhibit properties differently according to contents of carbohydrate, protein, and fat. The spectral signal refers to a signal obtained by sequentially arranging components of light present in an object, that is, a food according to a wavelength. According to one example, the spectral signal may have a wavelength band of 650 nm or more, for example, in a range between 887 nm to 1722 nm.

Referring to FIG. 1, the food information managing apparatus 100 according to one embodiment may include at least one of a spectral information acquisition unit 110, a learning unit 120, a database 130, and a food information providing unit 140. Hereinafter, each component will be described.

The spectral information acquisition unit 110 may acquire a spectral signal for food and caloric nutrient information corresponding to the spectral signal. The food may include at least one of standard model food and reference food (that is, actual food). Accordingly, the spectral information acquisition unit 110 may include a standard model food spectral information acquisition unit 112 and a reference food spectral information acquisition unit 114.

The standard model food spectral information acquisition unit 112 may acquire caloric nutrient information of the standard model food and information on a spectral signal corresponding to the caloric nutrient information. The standard model food may refer to food processed for an experiment in which each caloric nutrient of carbohydrate, protein, and fat varies in a predetermined unit, for example, in every 5%. For a more specific example, standard model food 1 may include carbohydrate:protein:fat at the ratio of 5%:0%:0% and have spectral signal 1, standard model food 2 may include carbohydrate:protein:fat at the ratio of 5%:5%:0% and have spectral signal 2, standard model food 3 may include carbohydrate:protein:fat at the ratio of 5%:5%:5% and have spectral signal 3, standard model food 4 may include carbohydrate:protein:fat at the ratio of 10%:0%:0% and have spectral signal 4, and standard model food n may include carbohydrate:protein:fat at the ratio of m %:m %:m % and have spectral signal n.

The food including 5% of only carbohydrate like standard model food 1, including 5% of carbohydrate and 5% of protein like standard model food 2, including 5% of carbohydrate, 5% of protein, and 5% of fat like standard model food 3, or including 10% of only carbohydrate like standard model food 4 is rarely present. However, it is significant in that the standard model food is prepared in advance and a spectral signal thereof is acquired.

In other words, the standard model food spectral information acquisition unit 112 may acquire information on changes of the spectral signal according to a concentration of each caloric nutrient. Accordingly, information on spectral signals synthesized through a combination of caloric nutrients may be acquired even for food that doesn't exist in nature. Then, the information acquired by the standard model food spectral information acquisition unit 112 may be used to construct the database 130 so as to have highly reliability.

The reference food spectral information acquisition unit 114 may acquire caloric nutrient information on reference food and information on a spectral signal corresponding to the caloric nutrient information. The reference food may refer to actual food present in nature, such as carrot, cabbage, sugar, and corn. The information acquired by the reference food spectral information acquisition unit 114 may also be provided to the database 130.

The learning unit 120 may learn a new caloric nutrient combination and a spectral signal upon the combination, based on the information acquired by the spectral information acquisition unit 120. In other words, the learning unit 120 may learn a new caloric nutrient combination and a spectral signal upon the combination by using the caloric nutrient information of the standard model food and the spectral signal information thereof, and the caloric nutrient information of the reference food and the spectral signal information thereof.

The learning unit 120 may generate new food composed by combining new caloric nutrients through the caloric nutrient information of the standard model food and the spectral signal information thereof. For verification of learning, the learning unit 120 may newly generate, for example, food having caloric nutrient the same as caloric nutrient of food which is a previously acquired through the reference food spectral information acquisition unit 114. In other words, the spectral signal for a new food may have already been acquired.

The learning unit 120 may predict a spectral signal for the new food. The learning unit 120 may predict the spectral signal for the new food through various machine learning schemes. The learning unit 120 may compare the predicted spectral signal with a spectral signal previously acquired through the reference food spectral information acquisition unit 114. When an error is less than a predetermined criterion as a result of the comparison, the learning unit 120 may determine that the learning has been conducted properly. On the contrary, when the error is greater than the predetermined criterion, the learning unit 120 may modify the learning. In the above manner, the learning unit 120 may perform the machine learning based on the information acquired through the spectral information acquisition unit 110.

When finding out a learning approach to pass the predetermined criterion, the learning unit 120 may synthesize an un-acquired caloric nutrient combination through the spectroscopic information acquisition unit 110. Accordingly, the learning unit 120 may predict a spectral signal for the synthesized caloric nutrient combination using the learning approach. In other words, the learning unit 120 may predict the relationship between a concentration value of the caloric nutrient and the spectral signal. Then, the learning unit 120 may provide information on the synthesized caloric nutrient combination, that is, concentration information of carbohydrate, protein and fat, and the predicted spectral signal information to the database 130 as a pair.

The database 130 may store, in pairs, the caloric nutrient concentration values and the spectral signal therefor acquired by the spectral information acquisition unit 110, and may also store, in pairs, the caloric nutrient concentration value and the corresponding spectral signal learned by the learning unit 120.

Accordingly, since information previously not provided by the spectral information acquisition unit 110 may be stored in the database 130, the analysis result of a spectral signal having high reliability may be provided.

In addition, after the caloric nutrients and the spectral signals of the standard model food in addition to the reference food are used for learning by the learning unit 120, and the learning results are stored in the database 130. Accordingly, vast efforts and costs required for constructing the database 130 can be significantly reduced.

Further, the database 130 may also store information on food name. For example, the database 130 may further acquire information on a food name in addition to the caloric nutrient information and the spectral signal, via the reference food spectral information acquisition unit 114.

The food information providing unit 140 may acquire a spectral signal for predetermined food and provide food information on the predetermined food. When only a spectral signal is acquired without knowing caloric nutrient information, the food information providing unit 140 may search the database 130 for a spectral signal having a high degree of matching with the acquired spectral signal. In other words, the food information providing unit 140 may retrieve caloric nutrient information paired with a spectral signal having the high degree of matching from the database 130. Accordingly, the food information providing unit 140 may provide information on food by using only the spectral signal.

When the spectral signal having a high degree of matching with the spectral signal for the predetermined food is not found in the database 130, the food information providing unit 140 may instruct the learning unit 120 to learn. In other words, the learning unit 120 may perform the learning by using the information acquired through the spectral information acquisition unit 110 according to the aforementioned method. Accordingly, a spectral signal that have not been learned in advance may be updated in the database 130 through additional learning.

When the spectral signal having a high degree of matching with the spectral signal for the predetermined food is found in the database 130, and information on food paired therewith is provided, the food information providing unit 140 may provide a different type of information on food by taking into consideration of the degree of matching. For example, when the degree of matching is higher than predetermined criterion A, in other words, when the degree of matching is excellent, the food information providing unit 140 may provide caloric nutrient information, such as information on a concentration or calories, and information on a food name. In contrast, when the degree of matching is higher than predetermined criterion B but lower than the criterion A, in other words, when the degree of matching is normal, the food information providing unit 140 may provide the caloric nutrient information but may omit the information on the food name. For example, the information on the food name may be provided as 'unknown'. Since the food name serves as information on food identity, an error may cause a secondary accident such as allergy. Accordingly, the secondary accident may be prevented by providing information on the food name only when the degree of matching is excellent.

The food information managing apparatus according to one embodiment of the present invention has been described with reference to FIG. 1. Hereinafter, a food information managing method according to a first embodiment of the present invention will be described with reference to FIGS. 2 to 6. It may also be implemented by the food information managing apparatus according to one embodiment described prior to the food information managing method according to the first embodiment of the present invention.

Figure 2:
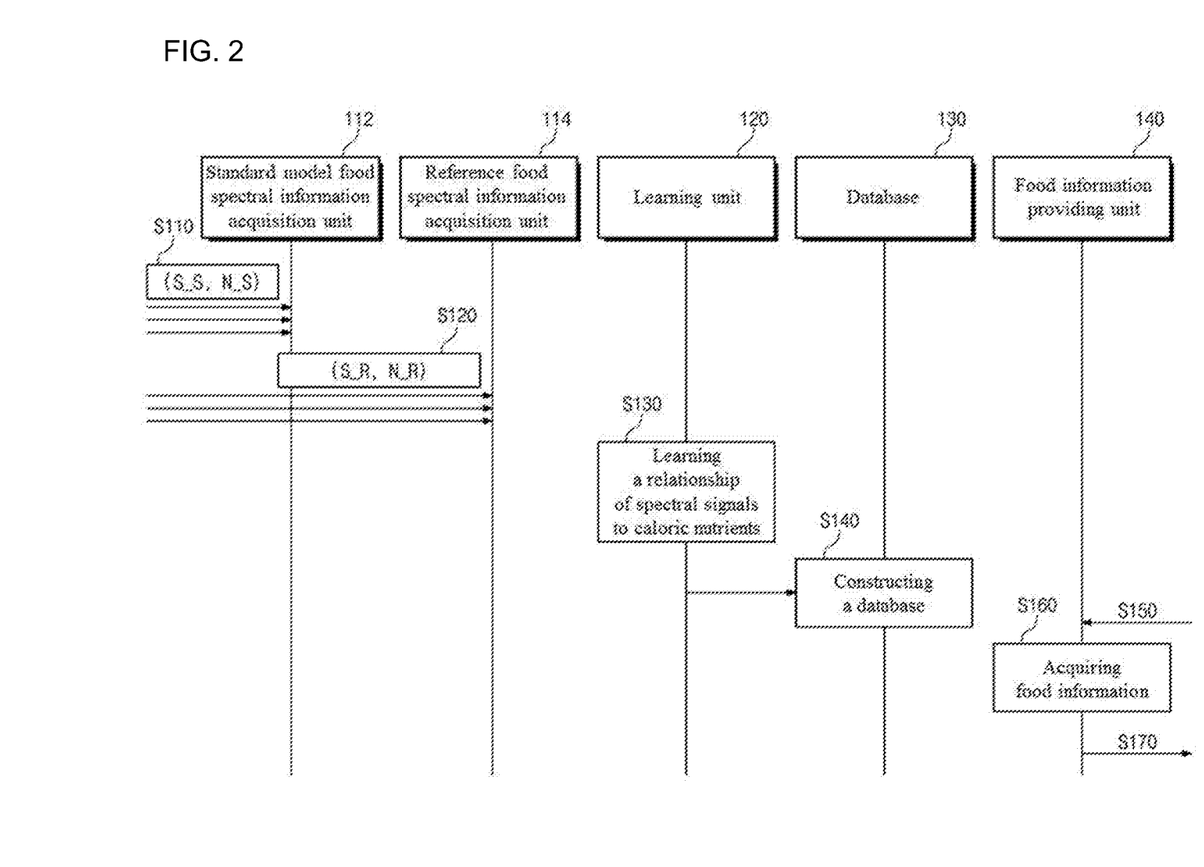
FIG. 2 shows a flowchart of a food information managing method according to a first embodiment of the present invention.

FIG. 2 shows a flowchart of a food information managing method according to the first embodiment of the present invention. FIGS. 3 to 6 are views for explaining in detail each step of the food information managing method according to the first embodiment of the present invention.

Referring to FIG. 2, the managing method for food information according to the first embodiment of the present invention may include at least one of a step in which the spectral information acquisition unit 110 acquires information on a caloric nutrient and a spectral signal (S110, S120), a step in which the learning unit 120 learns the relationship between the spectral signal and the caloric nutrient (S130), a step of building the database 130 (S140), and a step of providing food information (S150, S160 and S170). Hereinafter, each step will be described in detail.

Figure 3:
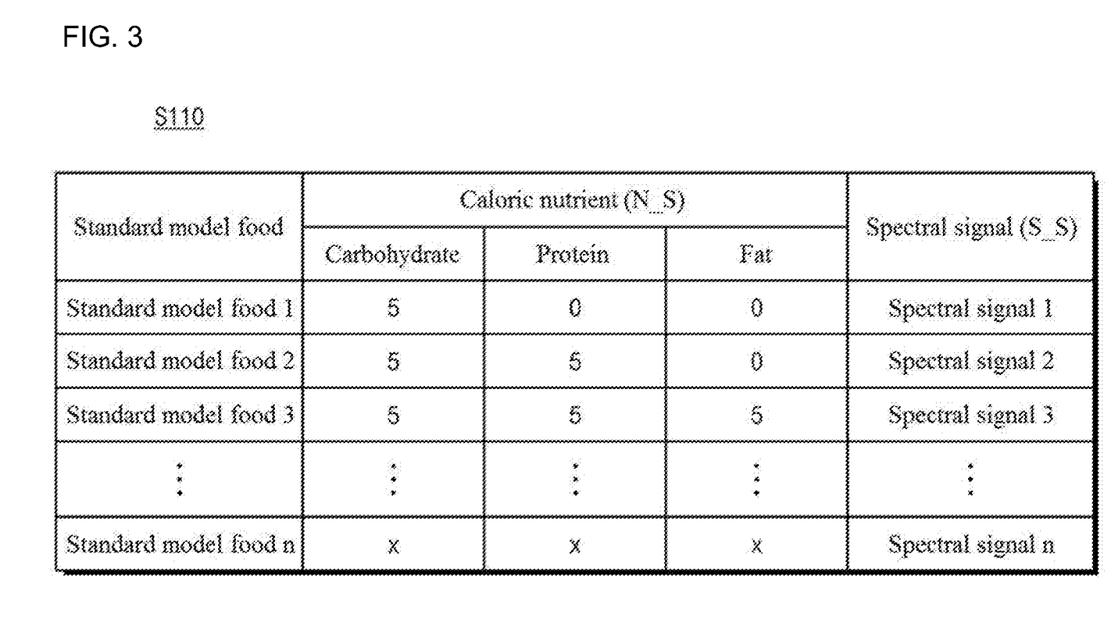
FIGS. 3 to 6 are views for illustrating in detail each step of the food information managing method according to the first embodiment of the present invention.

In step S110, as exemplarily shown in FIG. 3, the standard model food spectral information acquisition unit 112 may acquire a caloric nutrient (N_S) for standard model food and a corresponding spectral signal (S_S). The standard model food spectral information acquisition unit 112 may acquire spectral signals 1, 2, 3, . . . , and n for standard model food 1, 2, 3, . . . , and n. The standard model food spectral information acquisition unit 112 may provide the acquired information to the database 130.

Figure 4:
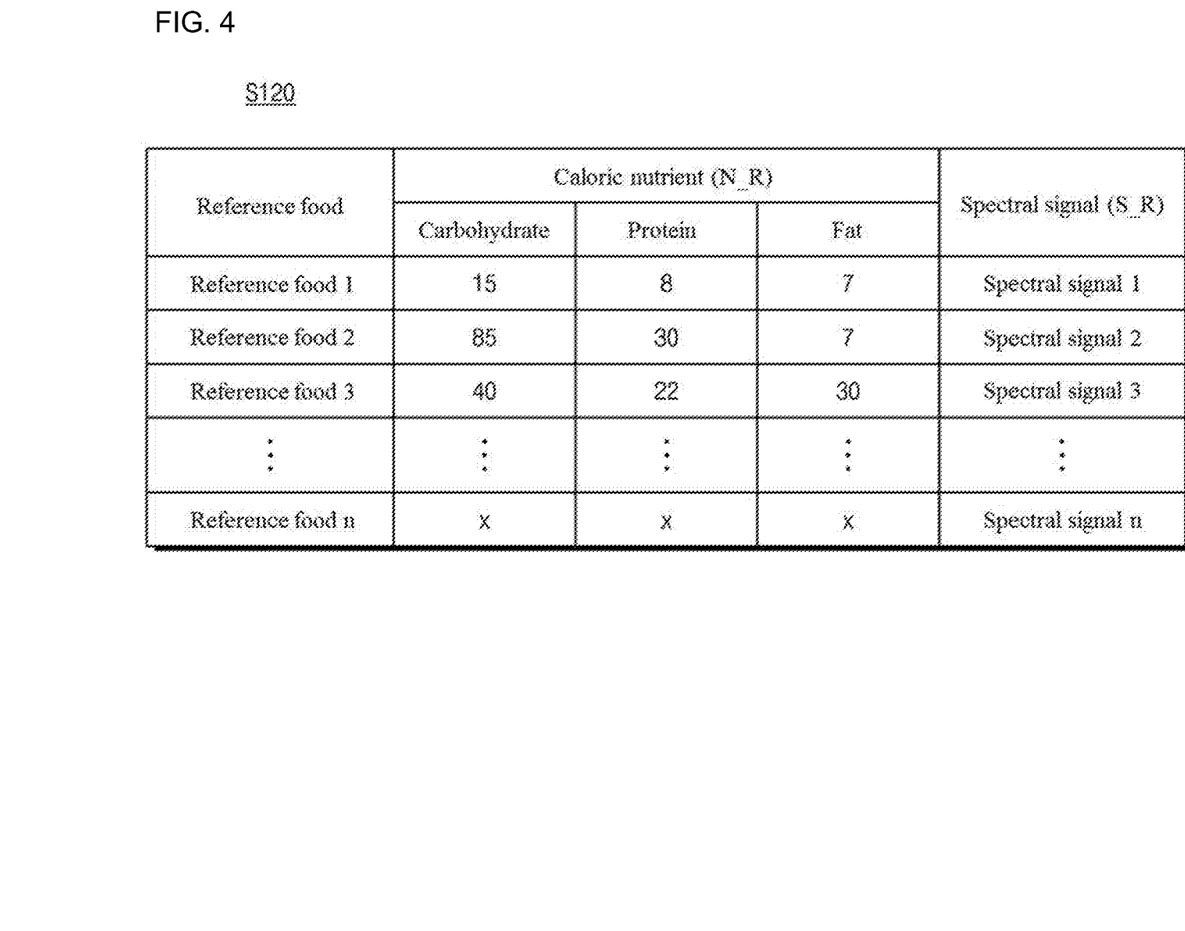

In step S120, as exemplarily shown in FIG. 4, the reference food spectral information acquisition unit 114 may acquire a caloric nutrient (S_R) for reference food and a corresponding spectral signal (S_R). The reference food spectral information acquisition unit 114 may acquire spectral signals 1, 2, 3, . . . , and n for reference food 1, 2, 3, . . . , and n. The reference food spectral information acquisition unit 114 may provide the acquired information to the database 130.

In step S130, the learning unit 130 may learn the relationship of the spectral signal with respect to the caloric nutrient based on the information acquired through the spectral information acquisition unit 110. Because the aforementioned spectral signal with reference to FIG. 3 has a caloric nutrient concentration value at 5% of intervals, a spectral signal learning is required for the sections at 5% of intervals. In addition, because the spectral signals described with reference to FIG. 4 have a physical limit to be applied to all food, a learning is required for the spectral signals.

Figure 5:
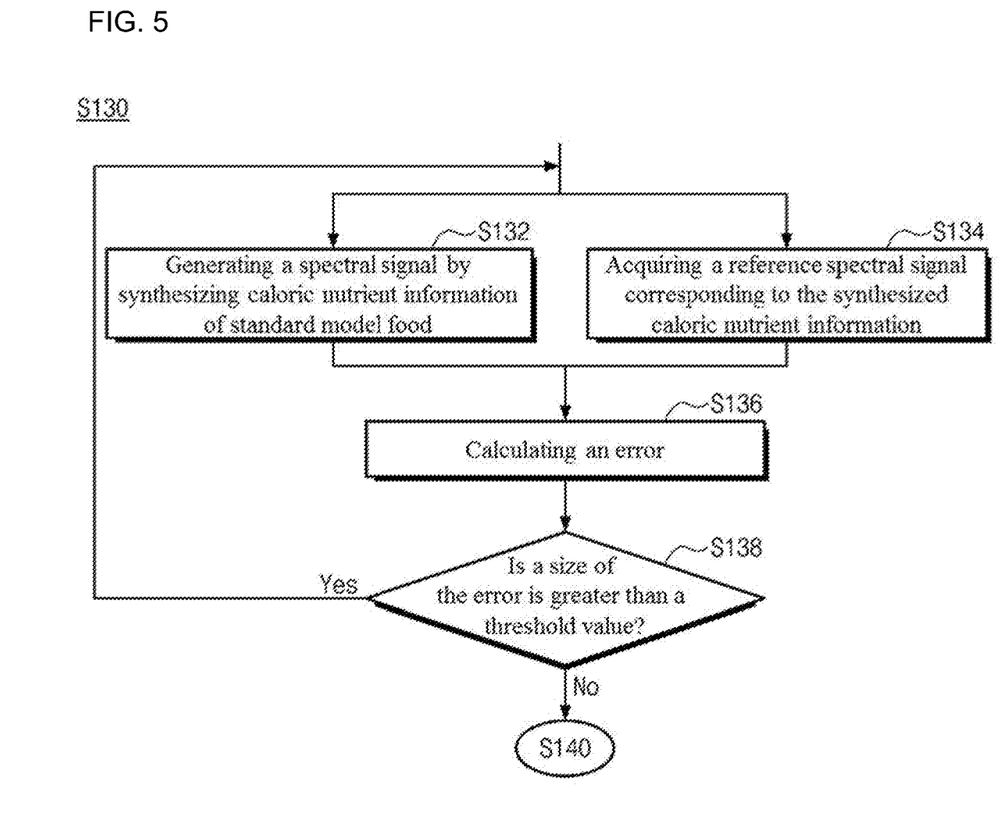

Step S130 will be described with reference to FIG. 5 for detailed description. Referring to FIG. 5, step S130 may include at least one of step S132 to step S138. Hereinafter, each step will be described.

In step S132, the learning unit 120 may predict the spectral signal by synthesizing caloric nutrient information of standard model food. For example, the learning unit 120 may adjust each individual caloric value of the standard model food to conform to a predetermined criterion of a caloric nutrient of the reference food. Accordingly, the learning unit 120 may synthesize caloric nutrients. Then, the learning unit 120 may predict a spectral signal corresponding to the synthesized caloric nutrient through the spectral signal (S_S) of the standard model food.

In step S134, the learning unit 120 may get the spectral signal corresponding to the synthesized caloric nutrient from the spectral signal (S_R) of the reference food.

In step S136, the learning unit 120 may compare the predicted spectral signal of step S132 with the actual spectral signal of step S134 and calculate an error.

In step S138, when the error of step S136 is greater than a predetermined threshold, step S132 and step S134 may be performed again from the beginning. In contrast, when the error of step S136 is less than or equal to the predetermined threshold, the learning approach of the learning unit 120 may be determined as being verified. Accordingly, a database construction may proceed.

Referring back to FIG. 2, in step S140, the learning unit 120 may conduct the learning in a verified learning approach. Accordingly, a combination of an un-acquired caloric nutrient may be randomly generated through the spectral information acquisition unit 110, and the spectral signal may be generated using the verified learning approach. The learning unit 120 may provide the learned pair of the caloric nutrient and the spectral signal to the database 130, and the database 130 may store the pair.

Figure 6:
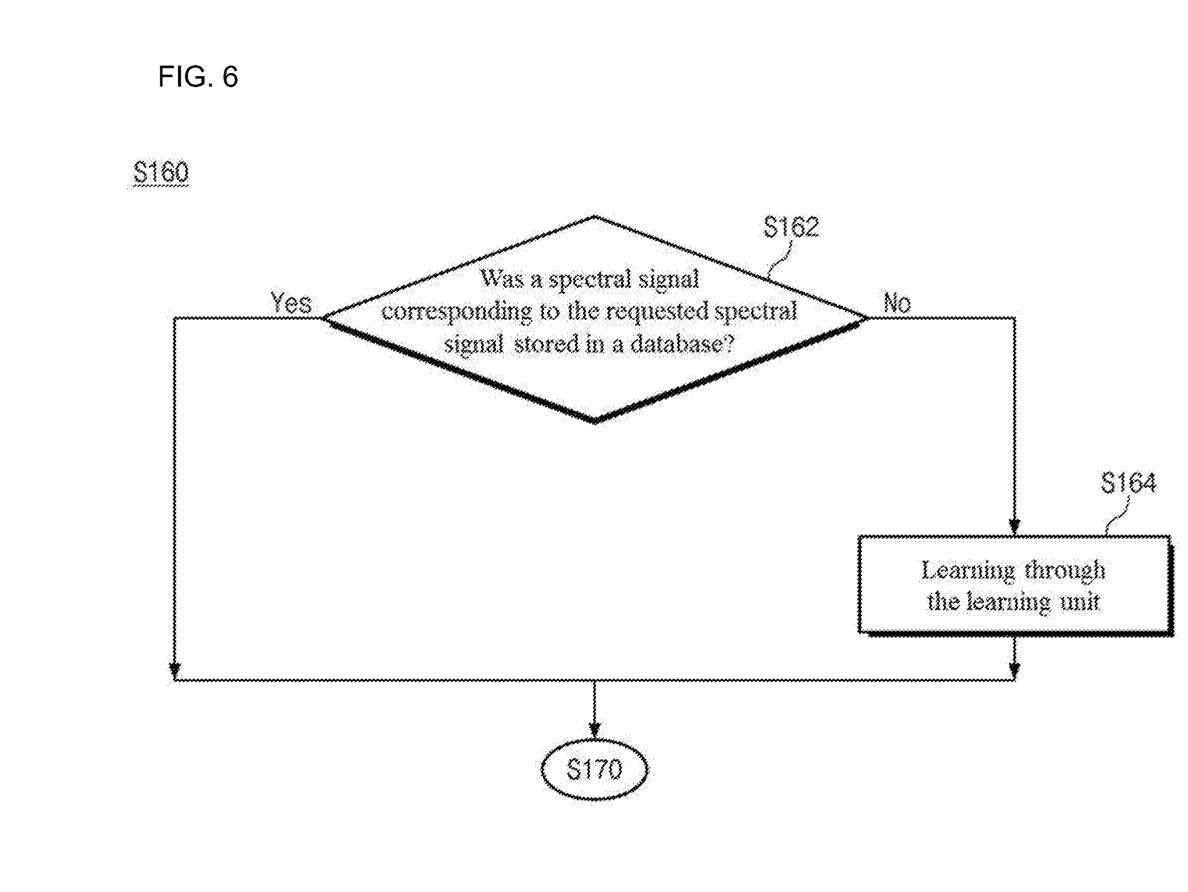

In step S150, the food information providing unit 140 may receive only a predetermined spectral signal. In this case, the food information providing unit 140 may provide information on food based on the predetermined spectral signal (step S160). More details will be described with reference to FIG. 6. Referring to FIG. 6, the food information providing unit 140 may compare the predetermined spectral signal with the spectral signal in the constructed database 130. When a spectral signal having a high matching degree is found in the database 130 as a result of the comparison, the food information providing unit 140 may provide corresponding food information such as information on a caloric nutrient and information on a food name (step S170). As described above, the information on a food name may be selectively provided in consideration of the degree of matching. When the spectral signal having a high matching degree is not found in the database 130 as a result of the comparison, the food information providing unit 140 may instruct the learning unit 120 to re-learn. Accordingly, the learning unit 120 may seek a new learning approach (step S164). Afterward, when the new learning approach is found, the food information providing unit 140 may provide food information, and the learning unit 120 may apply the new learning approach to conduct an additional learning.

The managing apparatus for food information and the managing method for food information according to the embodiments of the present invention have been described with reference to FIGS. 1 to 6. In the preceding description, it has been assumed that the learning unit 120 conducted the learning by using all of information obtained from each of the standard model food spectral information acquisition unit 112 and the reference food spectral information acquisition unit 114. In contrast, the learning may be conducted only using the information obtained from the reference food spectral information acquisition unit 114, excluding the information obtained from the standard model food spectral information acquisition unit 112.

Hereinafter, a managing apparatus for food information and a managing method for food information according to a second embodiment of the present invention will be described with reference to FIGS. 7 to 9. When the second embodiment of the present invention is described, the description overlapped with the first embodiment described with reference to FIGS. 1 to 6 may be omitted.

Figure 7:
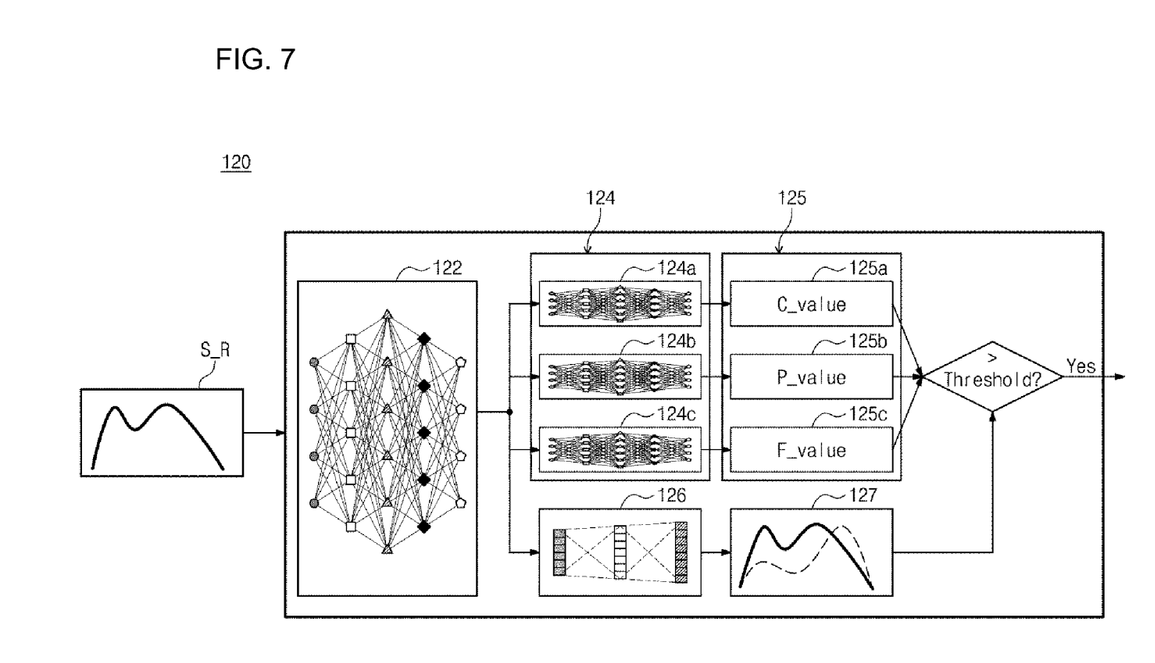
FIG. 7 is a view for explaining a block diagram of a food information managing apparatus according to a second embodiment of the present invention.

FIG. 7 is a view for explaining a block diagram of a food information managing apparatus according to the second embodiment of the present invention.

Referring to FIG. 7, the learning unit 120 according to the second embodiment of the present invention may include a learning network including a common network 122, a caloric nutrient-specific network 124, and a verification network 126. Hereinafter, unless otherwise specified, the learning unit 120 refers to a learning unit according to the second embodiment.

According to an embodiment of the present invention, the learning unit 120 may learn the relationship between a caloric nutrient and a spectral signal by using the information on the caloric nutrient and the spectral signal obtained through the spectral information acquisition unit 110, in which a neural network learning may be performed. The learning unit 120 may use only the information from the standard model food spectral information acquisition unit 112, or may use only the information from the reference food spectral information acquisition unit 114. Hereinafter, for convenience of description, it is assumed that the learning unit 120 is provided with the spectral signal S_R of the reference food.

The learning unit 120 may include the common network 122. The common network 122 may be formed of a neural learning network, and may include a plurality of layers including a plurality of nodes. The common network may receive the spectral signal S_R of the reference food, and extract common properties shared with the caloric nutrient-specific network 124. According to an embodiment of the present invention, the common network 122 may remove a noise from the spectral signal S_R of the reference food.

The common network 122 may include a plurality of layers for functional implementation, in which the number of nodes may increase and then decrease in a direction from the layer receiving the spectral signal S_R of the reference food to the caloric nutrient-specific network 124. In other words, the number of nodes of the last layer (the right layer of the common network 122 in FIG. 7) constituting the common network 122 may be less than the number of nodes of an immediately previous layer of the last layer. Accordingly, the common network 122 may provide a result in a compressed form. Accordingly, amounts of computation of subsequent networks may be reduced.

The last layer of the common network 122 may be connected to a joint layer 123. The joint layer 123 may be connected to the caloric nutrient-specific network 124 and the verification network 126.

The verification network 126 may receive the result of the common network 122 from the joint layer 123. The verification network 126 may inversely generate a spectral signal based on the received result. In other words, the number of nodes may gradually increase from a front layer to a rear layer of the verification network 126. In another aspect, when the joint network 123 provides an encoded result, the verification network 126 may decode the encoded result. Accordingly, the verification network 126 may generate a spectral signal by decoding the encoded result.

The spectral signal generated from the verification network 126 may be provided to the verification unit 127. The verification unit 127 may determine the degree of matching between the spectral signal S_R inputted to the common network 122 and the spectral signal decoded from the verification network 126 in various ways. For example, the verification unit 127 may determine the degree of matching between an area of the spectrum signal S_R inputted to the common network 122 and an area of the spectrum signal decoded from the verification network 126. In contrast, the verification unit 127 may determine the degree of matching between a waveform of the spectrum signal S_R inputted to the common network 122 and a waveform of the spectrum signal decoded from the verification network 126. The waveform comparison may be valid because it can accurately identify a case in which weight learning is insufficient between layer nodes of the common network 122.

When at least one degree of matching is higher than a predetermined criterion, the verification unit 127 may authenticate the learning approach of the common network 122. For example, when both of the area and the waveform are higher than the predetermined criterion, the verification unit 127 may authenticate the learning approach of the common network 122. In contrast, when all degrees of matching are less than or equal to the predetermined criteria, the verification unit 127 may retrain the common network 122. Accordingly, the relationship between nodes constituting the common network 122 may be reset.

The caloric nutrient-specific network 124 may receive the result of the common network 122 from the joint network 123. The caloric nutrient-specific network 124 may include carbohydrate network 124a, protein network 124b, and fat network 124c. The carbohydrate network 124a may provide a carbohydrate concentration corresponding to the spectral signal S_R inputted to the common network 122, the protein network 124b may provide a protein concentration corresponding to the spectral signal S_R inputted to the common network 122, and the local network 124c may provide a fat concentration corresponding to the spectral signal S_R inputted to the common network 122. According to an embodiment of the present invention, the number of nodes in each layer of the carbohydrate network 124a, the protein network 124b, and the fat network 124c may be constant.

A result value of the caloric nutrient-specific network 124 may be provided to a caloric nutrient result value providing unit 125. Specifically, the result value of the carbohydrate network 124a may be provided to a carbohydrate value providing unit 125a, the result value of the protein network 124b may be provided to a protein value providing unit 125b, and the result value of the fat network 124c may be provided to a fat value providing unit 125c.

The learning unit 120 may store the result value of the caloric nutrient result value providing unit 125 in the database 130 so as to be paired with the spectral signal. However, before storage, it may be confirmed whether the result has passed the above-described verification of the verification unit 127. When the result passes the verification of the verification unit 127, the learning unit 120 may store the result in the database 130. In contrast, when there is a result value provided from the caloric nutrient result value providing unit 125 without passing the verification of the verification unit 127, the common network 122 is required to be modified, so the resulting value may be discarded.

The learning unit 120 according to the second embodiment has been described. the spectral information acquisition unit 110, the database 130, and the food information providing unit 140 are the same as the above description according to the first embodiment except for the learning unit 120, and the detailed description will be omitted. The learning unit 120 according to the second embodiment may be preferable in that the learning can be conducted even when the number of inputted spectral signals is less, compared to the learning unit according to the first embodiment of the present invention. Accordingly, in the second embodiment, the input value from the spectral information acquisition unit 110 may be minimized. In addition, in the second embodiment, an example having only one of the standard model food spectral information acquisition unit 112 and the reference food spectral information acquisition unit 114 may be implemented The food information managing apparatus according to the second embodiment of the present invention have been described. Hereinafter, a food information managing method according to the second embodiment of the present invention will be described with reference to FIGS. 8 and 9.

Figure 8:
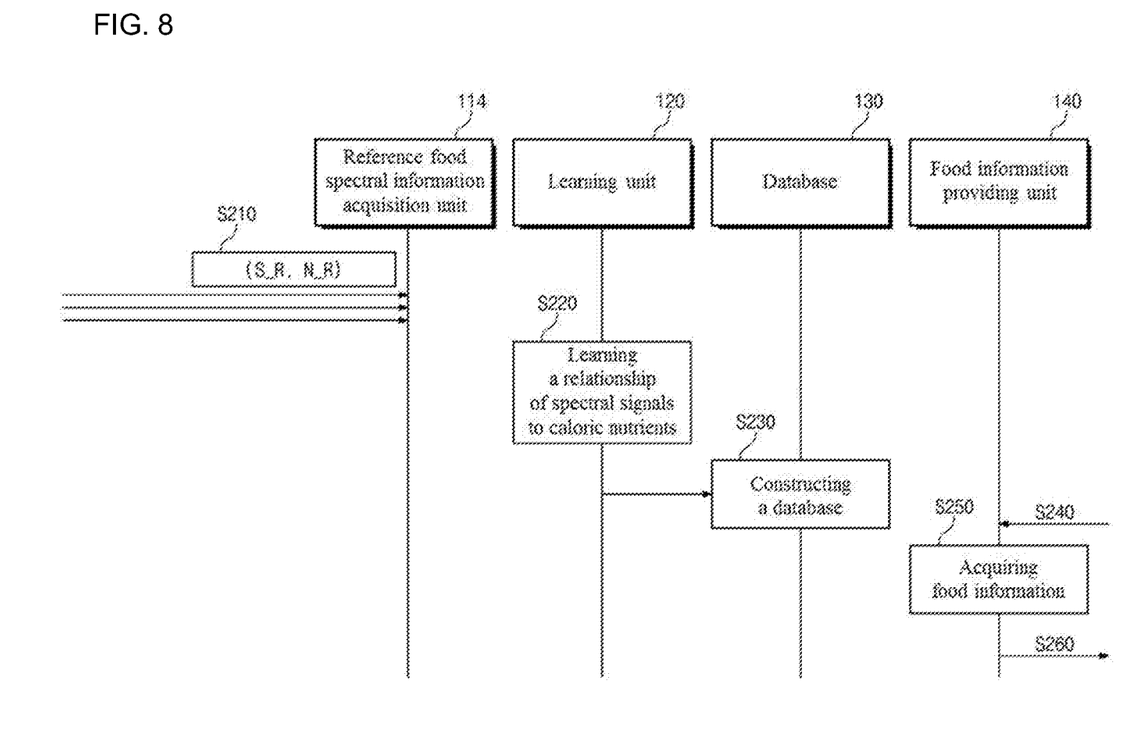
FIG. 8 is shows a flowchart of a food information managing method according to the second embodiment of the present invention.
Figure 9:
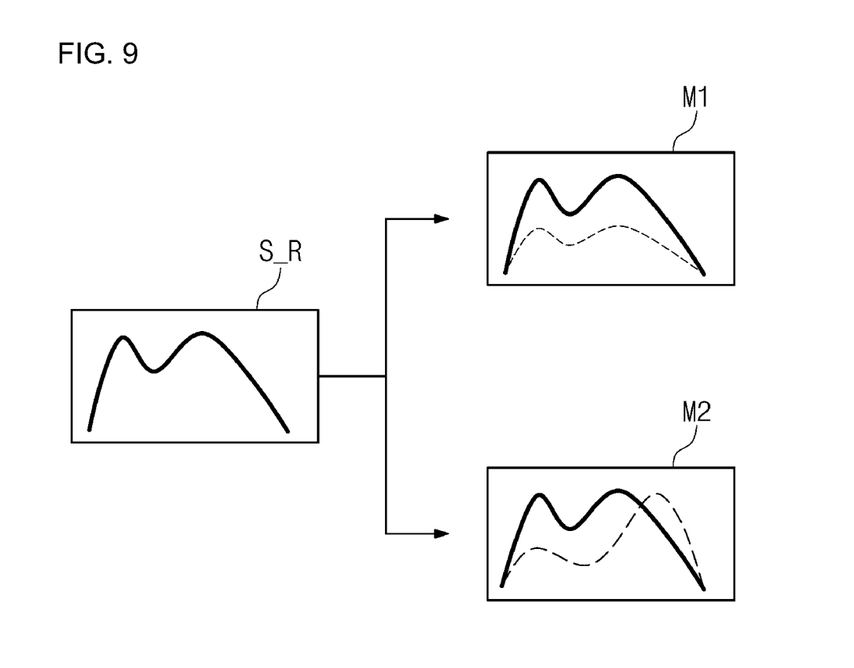
FIG. 9 is a view for explaining in detail each step of the food information managing method according to the second embodiment of the present invention.

FIG. 8 shows a flowchart of a food information managing method according to the second embodiment of the present invention. FIG. 9 is view for illustrating in detail each step of the food information managing method according to the second embodiment of the present invention.

In the second embodiment with reference to FIG. 8, the standard model food information acquisition unit 112 is omitted in order to emphasize the effect that the learning unit can conduct learning despite less input data.

Referring to FIG. 8, the managing method for food information according to the second embodiment of the present invention may include at least one of a step in which the reference food spectral information acquisition unit 114 acquires information on a caloric nutrient and a spectral signal (S210), a step in which the learning unit 120 learns the relationship between the spectral signal and the caloric nutrient (S220), and a step of constructing the database 130 (S230) and a step of providing food information (S240, S250 and S260). Hereinafter, each step will be described in detail. However, the description overlapped with the first embodiment will be omitted.

Since step S210 corresponds to step S120, the detailed description will be omitted.

In step S220, the learning unit 120 may learn the relationship between a spectral signal and a caloric nutrient. In other words, the learning unit 120 according to the second embodiment described with reference to FIG. 7 may learn the relationship between the spectral signal and the caloric nutrient through the learning network. In other words, the learning unit 120 may learn the information on the caloric nutrient based on the spectral signal acquired in step S210.

As described above, the learning unit 120 may provide the learning result in a compressed form through the common network 122. The learning result may be decoded by the verification network 126. Accordingly, the verification unit 127 may determine whether the learning of the common network 122 is properly performed. As shown in FIG. 9, in order to determine whether the learning is properly performed, the verification unit 127 may compare areas M1 and/or waveforms M2 between the spectral signal S_R inputted to the common network 122 and the spectral signal acquired from the verification network 126.

When the degree of matching is greater than a predetermined criterion as a result of the comparison, the verification unit 127 may determine that the learning of the common network 122 is properly performed. For convenience of description, when both of the area criterion and the waveform criterion match more than the predetermined criteria, it is assumed that the learning of the common network 122 is properly performed.

In contrast, when the degree of matching is less than or equal to the predetermined criterion as a result of the comparison, the verification unit 127 may retrain the common network 122. Accordingly, the relationship weights of the nodes of the common network 122 may be reset. In other words, the learning unit 120 may self-verify whether the learning is being properly performed.

Meanwhile, the caloric nutrient-specific network 124 may receive the learning result from the joint network 123 to perform the learning. The result of the caloric nutrient-specific network 124 may be provided to the caloric nutrient result value providing unit 125. The learning unit 120 may determine whether the result corresponds to the value having passed the verification of the verification unit 127 before storing the result value of the caloric nutrient result value providing unit 125 in the database 130.

Then, the learning unit 120 may determine whether the result value of the caloric nutrient result value providing unit 125 matches the caloric nutrient concentration value of the spectral signal S_R inputted to the common network 122. As a result of the determination, when the degree of matching is higher than a predetermined criterion, the learning result of the caloric nutrient-specific network 124 may be approved. In contrast, as a result of the determination, when the degree of matching is less than or equal to the predetermined criterion, the caloric nutrient-specific network 124 may be re-learned.

Accordingly, each node in the common network 122 and the caloric nutrient-specific network 124 may have a verified relationship (that is, a weight value).

The learning unit 120 may generate a caloric nutrient concentration value for a predetermined spectral signal through a verified learning network. Accordingly, the learning unit 120 may combine a new caloric nutrient and store the new caloric nutrient so as to be paired with a spectral signal corresponding to the new caloric nutrient in the database 130 based on the learning result (step S230).

Then, since steps S240 to S260 correspond to steps S150 to S170, respectively, the detailed description will be omitted.

The managing apparatus for food information and the managing method for food information according to the second embodiment of the present invention have been described. For convenience of description, although the first embodiment and the second embodiment are described separately, the managing apparatus for food information may be provided to implement both of the first and second embodiments.

Although the present invention has been described in detail using exemplary embodiments, the scope of the invention is not limited to the specific embodiments, and shall be interpreted by the appended claims. In addition, it will be apparent that a person having ordinary skill in the art may carry out various deformations and modifications for the embodiments described as above within the scope without departing from the present invention.

What is claimed is:

1. A food information managing apparatus comprising:
   a standard model food spectral information acquisition unit for acquiring a standard spectral signal and caloric nutrient information of standard model food, wherein the standard model food is manufactured to have predetermined caloric nutrient information, and the caloric nutrient information refers to concentrations of carbohydrate, fat, and protein;
   a reference food spectral information acquisition unit for acquiring a spectral signal and caloric nutrient information of the reference food;
   a learning unit for learning a scheme of estimating a spectral signal of synthesized caloric nutrient information that is obtained by synthesizing the caloric nutrient information of the standard model food such that a difference between the estimated spectral signal and a spectral signal of a reference food corresponding to the synthesized caloric nutrient information is a predetermined criterion or below;
   a database for storing the spectral signal and the caloric nutrient information of the reference food, the spectral signal and the caloric nutrient information of the standard model food, the estimated spectral signal and the synthesized caloric nutrient information based on a learning result of the learning unit; and
   a food information providing unit for providing food information about specific food based on a comparison between a spectral signal of the specific food and data stored in the database,
   wherein when a degree of matching between the spectral signal of the specific food and the spectral signal of the reference food is higher than predetermined criterion A, the food information providing unit provides the food information including a name of the reference food,
   wherein when the degree of matching between the spectral signal of the specific food and the spectral signal of the reference food or the estimated spectral signal is higher than predetermined criterion B but lower than the criterion A, the food information providing unit provides the food information including the caloric nutrient information of the reference food or the synthesized caloric nutrient information without the name of the reference food, and
   wherein the reference food refers to a single natural food item.

2. The food information managing apparatus of claim 1, wherein the food information providing unit generates new caloric nutrient information corresponding to the spectral signal of the specific food through the learning unit when there is no match for the spectral signal of the specific food in the database.

3. A food information managing method comprising:
   a standard model food spectral information acquisition step of acquiring a standard spectral signal and caloric nutrient information of standard model food, wherein the standard model food is manufactured to have predetermined caloric nutrient information, and the caloric nutrient information refers to concentrations of carbohydrate, fat, and protein;
   a reference food spectral information acquisition step of acquiring a spectral signal and caloric nutrient information of the reference food;
   a learning step of learning a scheme of estimating a spectral signal of synthesized caloric nutrient information that is obtained by synthesizing the caloric nutrient information of the standard model food such that a difference between the estimated spectral signal and a spectral signal of a reference food corresponding to the synthesized caloric nutrient information is a predetermined standard or below;
   a database construction step of storing the spectral signal and the caloric nutrient information of the reference food, the spectral signal and the caloric nutrient information of the standard model food, the estimated spectral signal and the synthesized caloric nutrient information based on a result of the learning step; and
   a food information providing step of providing food information about specific food based on a comparison between a spectral signal of the specific food and data stored in the database,
   wherein the food information providing step comprises:
   when a degree of matching between the spectral signal of the specific food and the spectral signal of the reference food or the estimated spectral signal is higher than predetermined criterion A, providing the food information including a name of the reference food, and
   wherein when the degree of matching between the spectral signal of the specific food and the spectral signal of the reference food or the estimated spectral signal is higher than predetermined criterion B but lower than the criterion A, providing the food information including the caloric nutrient information of the reference food or the synthesized caloric nutrient information without the name of the reference food, and
   wherein the reference food refers to a single natural food item.

4. A food information managing apparatus comprising:
   a reference food spectral information acquisition unit for acquiring information on a spectral signal corresponding to reference food and a caloric nutrient information of the reference food, wherein the caloric nutrient information refers to concentrations of carbohydrate, fat, and protein;

a learning unit for learning a relationship between the spectral signal and the caloric nutrient information through a learning network;

a database for storing the spectral signal and the caloric nutrient information of the reference food, and an estimated spectral signal of newly synthesized caloric nutrient information that is synthesized based on a learning result of the learning unit; and a food information providing unit for providing food information about specific food based on a comparison between a spectral signal of the specific food and data stored in the database, wherein when a degree of matching between the spectral signal of the specific food and the spectral signal of the reference food is higher than predetermined criterion A, the food information providing unit provides the food information including a name of the reference food, and wherein when the degree of matching between the spectral signal of the specific food and the spectral signal of the reference food or the estimated spectral signal is higher than predetermined criterion B but lower than the criterion A, the food information providing unit provides the food information including the caloric nutrient information of the reference food or the synthesized caloric nutrient information without the name of the reference food, and wherein the reference food refers to a single natural food item.

5. The food information managing apparatus of claim 4, wherein the learning network includes a common network that receives and processes the spectral signal of the reference food inputted to the common network, and a caloric nutrient-specific network following the common network and composed of a plurality of networks respectively corresponding to individual caloric nutrients, wherein a joint layer is located between the common network and the caloric nutrient-specific network, and a number of nodes in the joint layer is less than a number of nodes in a layer prior to the joint layer, wherein the joint layer is connected to a verification network, the verification network inversely generates the inputted spectral signal based on a result from the common network, and the learning unit retrains the common network when a degree of matching between the inputted spectral signal and the inversely generated spectral signal is a predetermined criterion or below.

6. The food information managing apparatus of claim 5, wherein the learning unit determines the degree of matching between the inputted spectral signal and the reversely generated spectral signal based on a waveform.

* * * * *